United States Patent

Prossel et al.

Patent Number: 6,107,500
Date of Patent: Aug. 22, 2000

[54] PROCESS FOR THE PREPARATION OF MIXTURES OF SORBITOL MONOESTERS, SORBITOL DIESTERS AND PARTIAL GYCERIDES

[75] Inventors: Günter Prossel, Burgkirchen; Bernd Papenfuhs, Obertshausen, both of Germany

[73] Assignee: Clariant GmbH, Frankfurt, Germany

[21] Appl. No.: 09/107,683

[22] Filed: Jun. 30, 1998

[30] Foreign Application Priority Data

Jul. 1, 1997 [DE] Germany .......................... 197 27 950

[51] Int. Cl.$^7$ ........................................................ C11C 1/00
[52] U.S. Cl. ........................... 554/169; 554/163; 554/167
[58] Field of Search .................... 554/167, 163, 554/169

[56] References Cited

FOREIGN PATENT DOCUMENTS

| | | |
|---|---|---|
| 108999 | 5/1984 | European Pat. Off. . |
| 2313543 | 10/1973 | Germany . |
| 966541 | 8/1964 | United Kingdom . |

OTHER PUBLICATIONS

European Search Report, Oct. 1998.
Derwent Patent Family Report and/or Abstract, 1998.

Primary Examiner—Deborah D. Carr
Attorney, Agent, or Firm—Miles B. Dearth; Scott E. Hanf

[57] ABSTRACT

A process for the preparation of mixtures which comprise mostly sorbitol monoesters, sorbitol diesters and partial glycerides, sorbitol being reacted with triglycerides in the presence of at least one alkaline catalyst, is described, wherein the cocatalyst used for the reaction is:

a) a part amount of the product of the above reaction as a self-emulsifier and/or b) an amidoamine of the following formula (I)

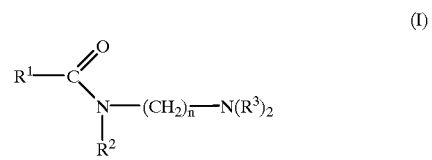

in which in which: $R^1$ is an alkyl or alkenyl group having 6 to 13 carbon atoms, $R^2$ is an alkyl group having 1 to 6 carbon atoms or an H atom, $R^3$ is an alkyl group having 1 to 6 carbon atoms and n is a number from 1 to 6. The novel process gives purer products and leads to a considerably improved space/time yield.

5 Claims, No Drawings

PROCESS FOR THE PREPARATION OF MIXTURES OF SORBITOL MONOESTERS, SORBITOL DIESTERS AND PARTIAL GYCERIDES

The invention relates to an economical process for the improved preparation of mixtures of sorbitol monoesters, sorbitol diesters and partial glycerides. Fatty acid monoglycerides and fatty acid diglycerides are often used as emulsifiers in the cosmetics sector and also in foodstuffs. Partial glycerides are usually obtained by transesterification of triglycerides with glycerol.

DE-A-23 13 543 describes a process for reacting triglycerides with sorbitol, but this is not satisfactory in respect of the purity of the products.

EP-B-1 08 999 discloses a process for the preparation of carboxylic acid esters of hexitols, a mixture of hexitol and carboxylic acid being reacted in the presence of an alkaline catalyst at a temperature of 210 to 250° C., while passing an inert gas through it, and the water formed being removed with the aid of a separator. A disadvantage of this process is that, under the drastic reaction conditions, water is split off to form anhydrohexose esters, which are cyclized in high proportions. The carboxylic acid hexose esters thus obtained accordingly have OH numbers which in all instances are too low.

An essential aim of the present invention was to determine mild reaction conditions under which almost exclusively noncyclic sorbitol esters are formed, i.e. the formation of anhydrosorbitol esters is avoided. The reaction of a triglyceride with sorbitol is a partial alcoholysis of the triglyceride under alkaline catalysis, with simultaneous esterification of the sorbitol.

Alkaline catalysts which can be used are alkali metal hydroxides and carbonates and alkali metal alcoholates or else high-boiling tertiary amines. Triglycerides which are used are coconut fat, palm oil, palm kernel oil, rapeseed oil, soybean oil and sunflower oil, in each case in refined quality and—preferably—in hydrogenated quality. Most experiments were carried out with refined and/or hydrogenated coconut fat. For easier handling, catalysts such as alkali metal alcoholates in alcoholic solution or potassium carbonate in aqueous solution can be added to the mixture of the starting materials. These solvents can be removed completely by heating up to 80 to 100° C. in vacuo before the actual reaction. The reaction is carried out under nitrogen as the inert gas.

At a molar ratio of sorbitol to triglyceride of 1:1 and an amount of catalyst of 0.5 to 2.0% by weight, based on the mixture of the starting materials, a reaction time of 10 to 20 hours at 140 to 150° C. is typically necessary for complete reaction. Surprisingly, it has now been found that by addition of a small amount of a reaction product, obtained as described above, to the mixture of sorbitol, triglyceride and catalyst, it is possible both to shorten the reaction time and to lower the reaction temperature. The active amount of reaction product added is 1 to 10% by weight, preferably 3 to 7% by weight, in each case based on the mixture employed. The amount of reaction product added is called "self-emulsifier" in the following text. By the addition according to the invention of self-emulsifier, the reaction temperature required can be lowered by on average about 20° C., it being possible for the reaction time to be halved on average at the same time. The lower reaction temperature leads to fewer by-products, i.e. purer products. The greatest advantage, however, is the saving in working time, because twice as much product is now obtained in the same preparation unit. The space/time yield is thus double de facto. Using potassium carbonate as the basic catalyst without a self-emulsifier, longer reaction times and/or higher reaction times than with sodium methanolate are generally required. This disadvantage is eliminated with a self-emulsifier. This is advantageous inasmuch as lighter-colored products are usually obtained with potassium carbonate.

It has furthermore been found that compounds of the formula (I)

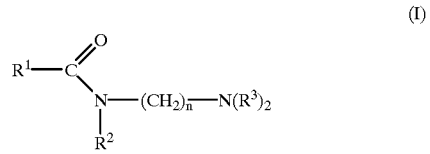

in which:
R$^1$ is an alkyl or alkenyl group having 6 to 13 carbon atoms,
R$^2$ is an alkyl group having 1 to 6 carbon atoms or an H atom,
R$^3$ is an alkyl group having 1 to 6 carbon atoms and
n is a number from 1 to 6, catalyze the reaction of sorbitol with triglycerides efficiently in a homogeneous phase. The amount of alkaline catalyst can be reduced drastically as a result, or an alkaline catalyst is no longer necessary at all. The amount of compound of the formula (I) is also 1 to 10, preferably 3 to 7% by weight, based on the mixture employed.

A 70% strength sorbitol syrup can also be used as the starting substance in the above process according to the invention. In this case, the water obtained is removed by brief heating at 120° C. under reduced pressure (about 30 mbar). After the sorbitol melt has been cooled to 80° C., the alkaline catalyst is first added, followed by the self-emulsifier and finally the liquid triglyceride. The actual reaction is then carried out at 115 to 135° C., preferably 120 to 130° C. The typical products are pasty to waxlike at room temperature, and colored beige to pale brown. The residual content of sorbitol is as a rule 4 to 5% and the content of anhydrosorbitol is 0.1 to 1.0%. The products prepared according to the invention are particularly mild on the skin and are therefore particularly suitable as emulsifiers for cosmetics formulations.

The novel process is illustrated by examples in the following text.

In these examples, Examples 1a, 2a, 3a, 4a and 5a correspond to the best prior art to date. Examples 1b, 2b, 3b, 4b and 5b describe the novel improved process with the addition of 5% by weight of self-emulsifier. In Example 3c, an amidoamine of the formula (I) is used, this also being employed in an amount of 5% by weight.

COMPARISON EXAMPLE 1a
(reaction of sorbitol with refined coconut fat)

660 g (1 mol) of refined coconut fat are initially introduced into a 2 l four-necked flask with a stirrer, condenser, nitrogen feed and thermometer and are heated to 120° C. 182 g (1 mol) of sorbitol and 8.4 g of NaOCH$_3$ (1% by weight, based on the total amount weighed out) are added and the mixture is heated to 140° C. According to analysis by gas chromatography (GC), the reaction has ended after 20 hours at 140° C. under N$_2$. The residual sorbitol content is 5.2% by weight. The reaction product formed is, in a quantitative yield, 850 g of a mixture of sorbitol monoester, sorbitol diester, fatty acid monoglyceride and fatty acid diglyceride as the main components having a melting range from 39 to 48° C.

| | |
|---|---|
| Iodine color number: | 5 |
| OH number: | 359 mg of KOH/g |
| Hydrolysis number: | 198 mg of KOH/g |

EXAMPLE 1b
(experiment with addition of 5% of self-emulsifier)

The procedure corresponds to Example 1a, with an addition of 43 g of self-emulsifier (5% by weight, based on the total amount weighed out) to the reaction mixture. According to GC analysis, the reaction has ended after 7 hours at 120° C. under $N_2$. The residual sorbitol content is 5.0% by weight. The reaction product formed is, in a quantitative yield, 893 g of a sorbitol ester/partial glyceride mixture having a melting range from 39 to 47° C.

| | |
|---|---|
| Iodine color number: | 4 |
| OH number: | 355 mg of KOH/g |
| Hydrolysis number: | 197 mg of KOH/g |

Comparison Example 2a
(reaction of sorbitol with hydrogenated coconut fat)

In a corresponding manner to that described in Example 1a, in this example 655 g (1 mol) of hydrogenated coconut fat, 182 g (1 mol) of sorbitol and 8.4 g of sodium methylate (1% by weight, based on the total amount weighed out) are employed. According to GC analysis, the reaction has ended after 11 hours at 140° C. under $N_2$. The residual sorbitol content is 5.3% by weight. The reaction product formed is, in a quantitative yield, 845 g of a sorbitol ester/partial glyceride mixture having a melting range from 35 to 42° C.

| | |
|---|---|
| Iodine color number: | 4 |
| OH number: | 380 mg of KOH/g |
| Hydrolysis number: | 197 mg of KOH/g |

EXAMPLE 2b
(experiment with addition of 5% of self-emulsifier)

The procedure corresponds to Example 2a, with an addition of 42 g of self-emulsifier (5% by weight, based on the total amount weighed out) to the reaction mixture. According to GC analysis, the reaction has ended after 7 hours at 120° C. under $N_2$. The residual sorbitol content is 5.2% by weight. The reaction product formed is, in a quantitative yield, 887 g of a sorbitol ester/partial glyceride mixture having a melting range from 35 to 42° C.

| | |
|---|---|
| Iodine color number: | 3 |
| OH number: | 383 mg of KOH/g |
| Hydrolysis number: | 197 mg of KOH/g |

Comparison Example 3a
(reaction of sorbitol with hydrogenated coconut fat, catalyst: $K_2CO_3$)

In a manner corresponding to that described in Example 1a, in this example 655 g (1 mol) of hydrogenated coconut fat, 182 g (1 mol) of sorbitol and 8.4 g of potassium carbonate (1% by weight, based on the total amount weighed out) are employed. According to GC analysis, the reaction has ended after 13 hours at 150° C. under $N_2$. The residual sorbitol content is 4.2% by weight. The reaction product formed is, in a quantitative yield, 845 g of a sorbitol ester/partial glyceride mixture having a melting range from 38 to 46° C.

| | |
|---|---|
| Iodine color number: | 4 |
| OH number: | 364 mg of KOH/g |
| Hydrolysis number: | 197 mg of KOH/g |

EXAMPLE 3b
(experiment with addition of 5% of self-emulsifier)

The procedure corresponds to Example 3a, with an addition of 42 g of self-emulsifier (5% by weight, based on the total amount weighed out) to the reaction mixture. According to GC analysis, the reaction has ended after 9.5 hours at 130° C. under $N_2$. The residual sorbitol content is 4.5% by weight. The reaction product formed is, in a quantitative yield, 887 g of a sorbitol ester/partial glyceride mixture having a melting range from 38 to 45° C.

| | |
|---|---|
| Iodine color number: | 4 |
| OH number: | 361 mg of KOH/g |
| Hydrolysis number: | 198 mg of KOH/g |

EXAMPLE 3c
(experiment with addition of 5% of coconut fatty acid amidopropyl-N,N-dimethylamine)

The procedure corresponds to Example 3a, with an addition of 42 g of coconut fatty acid amidopropyl-N,N-dimethylamine (5% by weight, based on the total amount weighed out) to the reaction mixture. According to GC analysis, the reaction has ended after 11 hours at 130° C. under $N_2$. The residual sorbitol content is 3.8% by weight. The reaction product formed is, in a quantitative yield, 887 g of a sorbitol ester/partial glyceride mixture having a melting range from 38 to 45° C.

| | |
|---|---|
| Iodine color number: | 4 |
| OH number: | 379 mg of KOH/g |
| Hydrolysis number: | 200 mg of KOH/g |

Comparison Example 4a
(reaction of sorbitol with palm kernel oil)

In a manner corresponding to that described in Example 1a, in this example 665 g (1 mol) of palm kernel oil, 182 g (1 mol) of sorbitol and 8.5 g of sodium methylate (1% by weight, based on the total amount weighed out) are employed. According to GC analysis, the reaction has ended after 12 hours at 130° C. under $N_2$. The residual sorbitol content is 4.2% by weight. The reaction product formed is, in a quantitative yield, 856 g of a sorbitol ester/partial glyceride mixture having a melting range from 40 to 48° C.

| | |
|---|---|
| Iodine color number: | 3 |
| OH number: | 382 mg of KOH/g |
| Hydrolysis number: | 190 mg of KOH/g |

EXAMPLE 4b
(experiment with addition of 5% of self-emulsifier)

The procedure corresponds to Example 4a, with an addition of 43 g self-emulsifier (5% by weight, based on the total amount weighed out) to the reaction mixture. According to GC analysis, the reaction has ended after 7 hours at 120° C. under $N_2$. The residual sorbitol content is 4.7% by weight. The reaction product formed is, in a quantitative yield, 899 g of a sorbitol ester/partial glyceride mixture having a melting range from 40 to 48° C.

| | |
|---|---|
| Iodine color number: | 3 |
| OH number: | 378 mg of KOH/g |
| Hydrolysis number: | 189 mg of KOH/g |

Comparison Example 5a
(reaction of sorbitol with soya bean oil)

In a manner corresponding to that described in Example 1a, in this example 876 g (1 mol) of soya bean oil, 182 g (1 mol) of sorbitol and 10.6 g of potassium carbonate (1% by weight, based on the total amount weighed out) are employed. According to GC analysis, the reaction has ended after 13 hours at 140° C. under $N_2$. The residual sorbitol content is 4.0% by weight. The reaction product formed is, in a quantitative yield, 1069 g of a sorbitol ester/partial glyceride mixture having a melting range from 17 23° C.

| | |
|---|---|
| Iodine color number: | 5 |
| OH number: | 283 mg of KOH/g |
| Hydrolysis number: | 155 mg of KOH/g |

EXAMPLE 5b
(experiment with addition of 5% of self-emulsifier)

The procedure corresponds to Example 5a, with an addition of 53 g of self-emulsifier (5% by weight, based on the total amount weighed out) to the reaction mixture. According to GC analysis, the reaction has ended after 7 hours at 120° C. under $N_2$. The residual sorbitol content is 4.3% by weight. The reaction product formed is, in a quantitative yield, 1122 g of a sorbitol ester/partial glyceride mixture having a melting range from 17 to 23° C.

| | |
|---|---|
| Iodine color number: | 4 |
| OH number: | 281 mg of KOH/g |
| Hydrolysis number: | 156 mg of KOH/g |

What is claimed is:

1. A process for the direct preparation of mixtures which comprise mostly sorbitol monoesters, sorbitol diesters and partial glycerides, avoiding the formation of cyclic sorbitol esters, by reaction of sorbitol with triglycerides in the presence of at least one alkaline catalyst, wherein the cocatalyst used for said reaction is:

a) a part amount of the product of the above reaction as a self-emulsifier and/or b) an amidoamine of the following formula (I)

$$R^1-\underset{\underset{R^2}{|}}{\overset{\overset{O}{\|}}{C}}-N-(CH_2)_n-N(R^3)_2 \quad (I)$$

in which:

$R^1$ is an alkyl or alkenyl group having 6 to 13 carbon atoms, $R^2$ is an alkyl group having 1 to 6 carbon atoms or an H atom, $R^3$ is an alkyl group having 1 to 6 carbon atoms and n is a number from 1 to 6.

2. The process for the preparation of mixtures as claimed in claim 1, wherein the amount of self-emulsifier and/or amidoamine of the formula (I) added is 1 to 10% by weight.

3. The process as claimed in claim 1, wherein the reaction is carried out at 115 to 135° C. under a nitrogen atmosphere.

4. The process as claimed in claim 2, wherein said amount of self-emulsifier and/or amidoamine added is 3 to 7% by weight.

5. The process as claimed in claim 3, wherein said reaction is carried out at 120 to 130° C., under a nitrogen atmosphere.

* * * * *